United States Patent [19]

Shade

[11] Patent Number: 5,780,450
[45] Date of Patent: Jul. 14, 1998

[54] USE OF ADENOSINE UPTAKE INHIBITORS FOR TREATING RETINAL OR OPTIC NERVE HEAD DAMAGE

[75] Inventor: Debra L. Shade, Arlington, Tex.

[73] Assignee: Alcon Laboratories, Inc., Fort Worth, Tex.

[21] Appl. No.: 560,776

[22] Filed: Nov. 21, 1995

[51] Int. Cl.[6] .................. A61K 31/70; A61K 31/505
[52] U.S. Cl. .................. 514/46; 514/528; 514/912
[58] Field of Search .................. 514/46, 256, 912

[56] References Cited

U.S. PATENT DOCUMENTS

| | | |
|---|---|---|
| 4,550,022 | 10/1985 | Garabedian et al. |
| 4,912,092 | 3/1990 | Gruber et al. |
| 5,075,290 | 12/1991 | Findley et al. |
| 5,236,908 | 8/1993 | Gruber et al. |
| 5,438,060 | 8/1995 | Miyazaki et al. |

FOREIGN PATENT DOCUMENTS

| | | |
|---|---|---|
| 0594223 A1 | 4/1994 | European Pat. Off. |
| WO 91/04032 | 4/1991 | WIPO |
| WO 93/23082 | 11/1993 | WIPO |
| WO 94/13275 | 6/1994 | WIPO |
| WO 95/33410 | 12/1995 | WIPO |

OTHER PUBLICATIONS

Dreyer et al., A proposed role for excitatory amino acids in glaucoma visual loss, *Investigative Ophthalmology and Visual Science*, vol. 34 (suppl.), p. 1504 (1993).

Shimada et al., Differences in ischemia–induced accumulation of amino acids in the cat cortex, *Stroke*, vol. 21, No. 10, pp. 1445–1451 (1990).

Drejer et al., Cellular origin of ischemia–induced glutamate release from brain tissue in vivo and in vitro, *Journal of Neurochemistry*, vol. 45, No. 1, pp. 145–151 (1985).

Benveniste et al. Elevation of the extracellular concentrations of glutamate and aspartate in rat hippocampus during transient cerebral ischemia monitored by intracerebral microdialysis, *Journal of Neurochemistry*, vol. 43, No. 5, pp. 1369–1374 (1984).

Beal, Mechanisms of exicitotoxicity in neurologic diseases, *FASEB Journal*, vol. 6, pp. 3338–3344 (1992).

Choi, Exicitotoxic cell death, *Journal of Neurobiology*, vol. 23, pp. 1261–1276 (1992).

Reif–Lehrer et al., Effects of monosodium glutamate on chick embryo retina in culture, *Investigative Ophthalmology and Visual Science*, vol. 14, No. 2, pp. 114–124 (1975).

Sisk et al., Histological changes in the inner retina of albino rats following intravitreal injection of monosodium L–glutamate, *Graefe's Archives of Clinical and Experimental Ophthalmology*, vol. 223, pp. 250–258 (1985).

Sattayasai et al., Morphology of quisqualate–induced neurotoxicity in the chicken retina, *Investigative Ophthalmology and Visual Science*, vol. 28, pp. 106–117 (1987).

David et al., Involvement of excitatory neurotransmitters in the damage produced in chick embryo retinas by anoxia and extracellular high potassium, *Experimental Eye Research*, vol. 46, pp. 657–662 (1988).

Tung et al., A quantitative analysis of the effects of excitatory neurotoxins on retinal ganglion cells in the chick, *Visual Neuroscience*, vol. 4, pp. 217–223 (1990).

Sucher et al., N–methyl–D–aspartate antagonists prevent kainate neurotoxocity in rat retinal ganglion cells in vitro, *Journal of Neuroscience*, vol. 11, pp. 966–971 (1991).

Siliprandi et al., N–methyl–D–aspartate–induced neurotoxicity in the adult rat retina, *Visual Neuroscience*, vol. 8, pp. 567–573 (1992).

Caprioli et al., Large retinal ganglion cells are more susceptible to excitotoxic and hypoxic injury than small cells, *Investigative Ophthalmology and Visual Science*, vol. 34 (suppl.), p. 1429 (1993).

Ramkumar, Adenosine, antioxidant enzymes and cytoprotection, *Trends in Pharmacological Sciences*, vol. 16, pp. 283–285 (1995).

Rudophi et al., Neuroprotective role of adenosine in cerebral ischemia, *Trends in Pharmacological Sciences*, vol. 13, pp. 439–445 (1992).

Deckert et al., Adenosine—an endogenous neuroprotective metabolite and neuromodulator, *Journal of Neural Transmission*, vol. 43 (suppl.), pp. 23–31 (1994).

Blazynski et al., Discrete Distributions of Adenosine Receptors in Mammalian Retina, *Journal of Neurochemistry*, vol. 54, No. 2, pp. 648–655 (1990).

Woods et al., Characterization of Adenosine $a_1$–Receptor Binding Sites in Bovine Retinal Membranes, *Experimental Eye Research*, vol. 53, pp. 325–331 (1991).

Braas et al., Endogenous adenosine and adenosine receptors localized to ganglion cells of the retina, *Proceedings of the National Academy of Science*, vol. 84, pp. 3906–3910 (1987).

Williams et al., Nucleoside Transport Sites in a Cultured Human Retinal Cell Line Established By Sv–40 T Antigen Gene, *Current Eye Research*, vol. 13, pp. 109–118 (1994).

*Ophthalmic Surgery: Principles of Practice*, Ed., G.L. Spaeth, W.B. Sanders Co. Philadelphia, PA, U.S.A., pp. 85–87 (1990).

Clanachan et al., Drug interactions with nucleoside transport systems, In: Gerlach E and Becker BF, eds. *Topics and Perspectives in Adenosine Research*, Springer–Verlag: Berlin, pp. 118–130 (1987).

Centelles et al., A model for adenosine transport and metabolism, *Biochemical Journal*, vol. 287, pp. 461–472 (1992).

Parkinson et al., Inhibitory effects of propentofylline on [$_3$H]adenosine influx, *Biochemical Pharmacology*, vol. 46, No. 5, pp. 891–896 (1993).

(List continued on next page.)

Primary Examiner—Zohreh Fay
Attorney, Agent, or Firm—Michael C. Mayo

[57] ABSTRACT

Compositions and methods directed to the use of adenosine uptake inhibitors for the treatment of retinal and optic nerve head damage following acute or chronic glaucoma, edema, ischemia, hypoxia or trauma are disclosed.

6 Claims, No Drawings

OTHER PUBLICATIONS

Vijayalakshmi et al., L1210/B23.1 cells express equilibrative, inhibitor-sensitive nucleoside transport and lack two parental nucleoside transport activities. *Journal of Biological Chemistry*, vol. 267, No. 24, pp. 16951–16956 (1992).

Deckert et al., (H–3)Dipyridamole and (H–3)Nitrobenzylthioinosine binding sites at the human parietal cortex and erythrocyte adenosine transporter: a comparison. *Life Sciences*, vol. 55, No. 21, pp. 1675–1682 (1994).

Betcher et al., Sodium–adenosine cotransport in brush–border membranes from rabbit ileum. *American Journal of Physiology*, vol. 259, pp. G504–510 (1990).

Yeung et al., Erythrocyte adenosine transport. A rapid screening test for cardiovascular drugs. *Journal of Pharmacological and Toxicological Methods*, vol. 30, No. 3, pp. 163–167 (1993).

Gu et al., L[$^3$–H]–adenosine, a new metabolically stable enantiomeric probe for adenosine transport systems in rat brain synaptoneurosomes. *Journal of Neurochemistry*, vol. 56, No. 2, pp. 548–552 (1991).

Braunagel et al., The potential role of adnosine in regulating blood flow in the eye. *J. Ocul. Pharmacol.*, vol. 4, No. 1, pp. 61–73 (1988).

Fern et al., Modulation of anoxic injury in CNS white matter by adenosine and interaction between adenosine and GABA. *J. Neurophysiol.*, vol. 72, No. 6, pp. 2609–2616 (1994).

Resul et al., Structure–activity relationships of prostaglandin analogues as ocular hypotensive agents. *Curr. Opin. Ther. Pat.*, vol. 3, No. 6, pp. 781–795 (1993).

Riva et al., Possible role of adenosine in the response of optic nerve head blood flow to neuronal stimulation. *Exp. Eye Res.*, vol. 55, No. suppl.1, sec. 278 (1992).

Vargas et al, Trombosis de la vena central de la retina. *Angiologia*, vol. 26, No. 3, pp. 112–116 (1974).

USE OF ADENOSINE UPTAKE INHIBITORS FOR TREATING RETINAL OR OPTIC NERVE HEAD DAMAGE

The present invention relates to the field of ophthalmology. In particular, the present invention relates to the treatment of retinal tissues. More specifically, the present invention discloses compositions and methods of using adenosine uptake inhibitors in the prevention or treatment of retinal and/or optic nerve head damage resulting from glaucoma, edema, trauma, ischemia or hypoxia.

BACKGROUND OF THE INVENTION

Many of the pathological changes in the retina and optic nerve head, including damage related to glaucoma, ischemia, hypoxia, edema or trauma, are believed to be at least partially mediated by excitatory amino acids such as glutamate. Indeed, the vitreal concentration of glutamate has been shown to be significantly increased in glaucomatous patients (Dreyer et al., *A proposed role for excitatory amino acids in glaucoma visual loss, Investigative Ophthalmology and Visual Science*, volume 34 (suppl.), page 1504 (1993)).

Massive release of excitatory amino acids is known to occur under conditions of cellular ischemia, hypoxia or other stresses (Shimada et al., *Differences in ischemia-induced accumulation of amino acids in the cat cortex, Stroke*, volume 21, pages 1445–1451 (1990)). Prolonged oxygen and nutrient deprivation, or other stress, leads to depolarization of neuronal cell membranes. Depolarization increases synaptic glutamate release and reduces glutamate uptake, resulting in elevated extracellular glutamate levels (Drejer et al., *Cellular origin of ischemia-induced glutamate release from brain tissue in vivo and in vitro, Journal of Neurochemistry,* volume 45, pages 145–151 (1985); and Benveniste et al. *Elevation of the extracellular concentrations of glutamate and aspartate in rat hippocampus during transient cerebral ischemia monitored by intracerebral microdialysis, Journal of Neurochemistry,* volume 43, pages 1369–1374 (1984)).

Increased extracellular glutamate concentration results in overstimulation of cells, a potentially lethal condition referred to as "excitotoxicity" (Beal, *Mechanisms of excitotoxicity in neurologic diseases, FASEB Journal,* volume 6, pages 3338–3344 (1992); and Choi, *Excitotoxic cell death, Journal of Neurobiology,* volume 23, pages 1261–1276 (1992)). The process of excitotoxicity has been extensively studied in the retina. Toxicity to retinal cells has been observed following (1) intravitreal injection of excitatory amino acids, (2) in vitro treatment of isolated retina with excitatory amino acids, and (3) exogenous application of glutamate to cultured retinal ganglion cells. This excitotoxicity has been shown to be inhibited by pretreatment with excitatory amino acid receptor antagonists.

Examples of references pertaining to retinal excitatory amino acid toxicity include:

Reif-Lehrer et al., *Effects of monosodium glutamate on chick embryo retina in culture, Investigative Ophthalmololgy and Visual Science,* volume 14, pages 114–124 (1975);

Sisk et al., *Histological changes in the inner retina of albino rats following intravitreal injection of monosodium L-glutamate, Graefe's Archives of Clinical and Experimental Ophthalmology,* volume 223, pages 250–258 (1985);

Sattayasai et al., *Morphology of quisqualate-induced neurotoxicity in the chicken retina, Investigative Ophthalmology and Visual Science,* volume 28, pages 106–117 (1987);

David et al., *Involvement of excitatory neurotransmitters in the damage produced in chick embryo retinas by anoxia and extracellular high potassium, Experimental Eye Research,* volume 46, pages 657–662 (1988);

Tung et al., *A quantitative analysis of the effects of excitatory neurotoxins on retinal ganglion cells in the chick, Visual Neuroscience,* volume 4, pages 217–223 (1990);

Sucher et al., *N-methyl-D-aspartate antagonists prevent kainate neurotoxocity in rat retinal ganglion cells in vitro, Journal of Neuroscience,* volume 11, pages 966–971 (1991);

Siliprandi et al., *N-methyl-D-aspartate-induced neurotoxicity in the adult rat retina, Visual Neuroscience,* volume 8, pages 567–573 (1992); and Caprioli et al., *Large retinal ganglion cells are more susceptible to excitotoxic and hypoxic injury than small cells, Investigative Ophthalmology and Visual Science,* volume 34 (suppl.), page 1429 (1993).

Adenosine has been shown to exert modulatory and protective effects on cells undergoing excitotoxic and/or ischemic stress. Its cytoprotective effects are linked to its stimulation of specific receptors on the cell surface. Three adenosine receptor subtypes, $A_1$, $A_2$, and $A_3$, have been identified in mammalian tissues to date, although others may also be present (Ramkumar, *Adenosine, antioxidant enzymes and cytoprotection, Trends in Pharmacological Sciences,* volume 16, pages 283–285 (1995)).

Binding of adenosine to its receptors initiates a cascade of events which may ultimately confer neuroprotection. For example, adenosine has been shown to (1) limit uncontrolled membrane depolarization, (2) maintain intracellular calcium homeostasis, and (3) reduce the release of neurotransmitters, including the excitatory amino acid glutamate (Rudolphi et al., *Neuroprotective role of adenosine in cerebral ischemia, Trends in Pharmacological Sciences,* volume 13, pages 439–445 (1992)). Furthermore, adenosine has been shown to induce glycogenolysis and enhance blood flow and oxygen supply, as well as increase both potassium efflux and chloride influx. More importantly, adenosine has been shown to increase energy supplies while decreasing energy demand during ischemic conditions (Deckert et al., *Adenosine—an endogenous neuroprotective metabolite and neuromodulator, Journal of Neural Transmission,* volume 43 (suppl.), pages 23–31 (1994)).

Adenosine receptors have been shown to exist in the retinas of various mammalian species including bovine, porcine, monkey, rat, guinea pig, mouse, rabbit and human (See, Blazynski et al., *Discrete Distributions of Adenosine Receptors in Mammalian Retina, Journal of Neurochemistry,* volume 54, pages 648–655 (1990); Woods et al., *Characterization of Adenosine $A_1$-Receptor Binding Sites in Bovine Retinal Membranes, Experimental Eye Research,* volume 53, pages 325–331 (1991); and Braas et al., *Endogenous adenosine and adenosine receptors localized to ganglion cells of the retina, Proceedings of the National Academy of Science,* volume 84, pages 3906–3910 (1987)).

Recently, Williams reported the observation of adenosine transport sites in a cultured human retinal cell line (Williams et al., *Nucleoside Transport Sites in a Cultured Human Retinal Cell Line Established By SV-40 T Antigen Gene, Current Eye Research,* volume 13, pages 109–118 (1994)).

Various pharmaceutical attempts have been made to exploit the cytoprotective effects of adenosine receptor stimulation. For example, adenosine receptor agonists, such as cyclohexyladenosine, have been used to stimulate the $A_1$ receptor, the subtype which moderates many of the protective actions of adenosine (Rudolphi et al., *Neuroprotective role of adenosine in cerebral ischemia, Trends in Pharmacological Sciences*, volume 13, page 439–445 (1992)). Other attempts at modulating adenosine action include adenosine deaminase inhibitors, such as pentostatin and conformycin, to increase extracellular adenosine. Further, U.S. Pat. No. 4,912,092 (Gruber et al.) discloses purine and adenyl derivatives useful as adenosine precursors for the enhancement of adenosine synthesis, and hence the increase of extracellular adenosine.

Adenosine uptake inhibitors have been proposed for various pharmaceutical treatments. For example European Patent Publication No. EP 0594223 A1 discloses use of combination therapy including adenosine uptake inhibitors for anti-viral treatment. U.S. Pat. No. 5,075,290 (Findley et al.) discloses adenosine uptake inhibitors for the treatment of obstructive sleep apnea and related snoring.

Adenosine uptake inhibitors also represent another approach to adenosine receptor modulation and hence cytoprotective therapy. WIPO Publication number WO 91/04032 discloses various adenosine modulators as well as certain uptake inhibitors for the protection of neural tissues especially in treating Parkinson's Disease, Alzheimer's Disease and Huntington's Disease. Nowhere in the art however, has it been disclosed to use adenosine uptake inhibitors for the acute or chronic prevention or treatment of retinal or optic nerve head damage resulting from glaucoma or various ischemic insults.

SUMMARY OF THE INVENTION

The present invention discloses adenosine uptake antagonists for the prevention, reduction or amelioration of chronic or acute retinal and/or optic nerve head damage related to glaucoma, hypoxia, ischemia, edema or trauma. The present invention discloses compositions for systemic, topical and intraocular administration of at least one adenosine uptake inhibitor in an amount effective to prevent or to treat retinal and/or optic nerve head tissue damage.

Methods are disclosed for the prevention or treatment of retinal and optic nerve head damage associated with glaucoma, hypoxia, ischemia, edema or trauma. Preferred methods include the systemic, topical or intraocular administration of an effective amount of an adenosine uptake inhibitor for treatment of retinal and/or optic nerve head damage.

DETAILED DESCRIPTION OF THE INVENTION

While Applicants do not wish to be bound by any theory, it is believed that adenosine is returned to the cytoplasm via both simple diffusion and carrier-mediated nucleoside transport systems. Simple diffusion is driven solely by the concentration gradient of nucleosides existing between the extra- and intracellular fluids. The rate of simple diffusion would therefore not be expected to be affected by agents which act as adenosine uptake inhibitors. On the other hand, carrier-mediated nucleoside transport, which can occur through either equilibrative or concentrative mechanisms, would be expected to be controllable.

Concentrative mechanisms involve active transport and are coupled to the movement of sodium ions across the cell membrane, allowing for transport of nucleosides against their concentration gradient. This type of transporter is termed "sodium-dependent." Conversely, equilibrative processes are sodium-independent, and may involve an antiport system in which extracellular adenosine is exchanged, for example, for intracellular inosine. Equilibrative processes appear to be the predominate form of adenosine transport expressed in brain tissue, although low levels of concentrative transporters have also been identified in some species (See: Clanachan et al., *Drug interactions with nucleoside transport systems*, In: Gerlach E and Becker B F, eds. *Topics and Perspectives in Adenosine Research*, Springer-Verlag: Berlin, pages 118–130 (1987), and Centelles et al., *A model for adenosine transport and metabolism, Biochemical Journal*, volume 287, pages 461–472 (1992)).

Nucleoside uptake systems are thus classified according to their sodium-dependence or independence. They may be further classified based on their sensitivity to the uptake inhibitor nitrobenzylthioinosine (NBMPR), as well as by their affinity for various nucleoside substrates. For example, at least two subtypes of equilibrative transporters have been identified: one, "es," which is equilibrative and NBMPR-sensitive and two, "ei" which is equilibrative but insensitive to NBMPR antagonism. Both the es and the ei carrier types are known to be adenosine permeable. Concentrative forms identified to date include "cif" (or N1), which is selective for formycin B, "cit" (or N2), which is selective for thymidine, and "cib," which transports a broad range of substrates, including adenosine. The concentrative forms do not appear to be NBMPR-sensitive (Parkinson et al., *Inhibitory effects of propentofylline on [$^3$H]adenosine influx, Biochemical Pharmacology*, volume 46, pages 891–896 (1993)).

Adenosine uptake inhibition, therefore, can be obtained by using an agent which will selectively block the action of membrane carrier proteins (e.g., es, ei, cib, or other yet-to-be identified subtypes) involved in transport of the nucleoside adenosine.

The present invention provides for compositions containing adenosine uptake inhibitors and methods of their use in treating acute or chronic retinal or optic nerve head damage resulting from glaucoma, edema, ischemia, hypoxia and trauma. Compounds useful in the present invention include all agents which inhibit the uptake or reabsorption of adenosine into the neural cells of ocular tissues. As used herein, "adenosine uptake inhibitor," or "AUI," refers to any agent which is efficacious in blocking adenosine transport into a cell. Such AUIs include those known compounds which have been shown to inhibit adenosine transport, their analogs and derivatives, as well as other AUIs which may be identified according to techniques herein described.

Examples of AUIs include:
dipyridamole;
propentofylline;
dilazep;
nitrobenzylthioinosine;
S-(4-nitrobenzyl)-6-thioguanosine;
S-(4-nitrobenzyl)-6-thioinosine;
iodohydroxy-nitrobenzylthioinosine;
mioflazine; and esters, amides and prodrugs thereof, and pharmaceutically acceptable salts thereof.

Several experimental techniques are known for the elucidation of AUIs. The affinity of AUI's for specific transporter subtypes can be determined by assaying their activity in cell lines which are known to selectively express only certain subtype(s). For example, the mouse leukemia cell strain, L1210/B23.1, expresses only the "es" subtype (Vijayalakshmi et al., *L1210/B23.1 cells express equilibrative, inhibitor-sensitive nucleoside transport and lack two parental nucleoside transport activities, Journal of Biological Chemistry*, volume 267, pages 16951–16956 (1992)). Sensitivity (or lack of) to NBMPR inhibition may also be used to ascertain the type of transporter present. For example, recent data indicates that human retinal cells express an NBMPR-sensitive transporter, and therefore are likely to possess either an es or an "es-like" subtype (Williams et al., *Nucleoside transport sites in a cultured human retinal cell line established by SV-40 T antigen gene, Current Eye Research*, volume 13, pages 109–118 (1994)).

The ability of potential AUIs to suppress transmembrane adenosine flux may be assessed by direct uptake experiments using a radioactively-labelled substrate (e.g. [$^3$H] adenosine). For example, cultured cells or isolated tissues of interest would be preincubated with or without increasing concentrations of potential AUIs, followed by exposure to the radiolabelled substrate, and in the presence or absence of a known inhibitor (such as NBMPR). After a predetermined period, the incubation media is removed and the cells or tissues are washed rapidly to eliminate unincorporated substrate. Total radioactivity remaining in the samples is then determined and used to establish dose-response curves.

The following publications contain examples of assays based on the preceeding discussion of AUI elucidation techniques, and are incorporated herein by reference to the extent they disclose assay methods for the elucidation of AUIs:

(1) Betcher et al., *Sodium-adenosine cotransport in brush-border membranes from rabbit ileum, American Journal of Physiology*, volume 259, pages G504–510 (1990);

(2) Yeung et al., *Erythrocyte adenosine transport. A rapid screening test for cardiovascular drugs, Journal of Pharmacological and Toxicological Methods*, volume 30, pages 163–167 (1993);

(3) Gu et al., *L[$^3$-H]-adenosine, a new metabolically stable enantiomeric probe for adenosine transport systems in rat brain synaptoneurosomes, Journal of Neurochemistry*, volume 56, pages 548–552 (1991); and (4) Parkinson et al., *Inhibitory effects of propentofylline on [$^3$-H]adenosine influx. A study of three nucleoside transport systems, Biochemical Pharmacology*, volume 46, pages 891–895 (1993).

An additional approach to the evaluation of potential AUI agents uses binding assays with high affinity probes, such as radiolabelled nitrobenzylthioinosine, and homogenates or purified plasma membranes from the cell/tissue (e.g. retina) of choice. In these assays, potential AUI agents are evaluated for their ability to compete with the radiolabelled probe for transporter binding sites, thus establishing the presence or absence of such sites. This affinity-binding technique further refines data obtained from the functional assays described previously, which cannot easily discriminate simple diffusion of substrate from that of carrier-mediated substrate transport. Therefore, results from these affinity-binding assays confirm the discovery of AUIs and represent preferred techniques for their elucidation.

The following publications contain examples of assays based on affinity-binding techniques for the elucidation of AUIs, as described above, and are incorporated herein by reference to the extent they disclose assay methods for the elucidation of AUIs:

(1) Williams et al., *Nucleoside transport sites in a cultured human retinal cell line established by SV-40 antigen gene, Current Eye Research*, volume 13, pages 109–118 (1994); and (2) Deckert et al., *(H-3)Dipyridamole and (H-3) Nitrobenzylthioinosine binding sites at the human parietal cortex and erythrocyte adenosine transporter—a comparison, Life Sciences*, volume 55, pages 1675–1682 (1994).

Using the above described techniques, other AUIs may become known, and are therefore, contemplated by the present invention and within the definition of AUI.

The AUIs may be contained in various types of pharmaceutical compositions, in accordance with formulation techniques known to those skilled in the art. For example, the compounds may be included in tablets, capsules, solutions, suspensions and other dosage forms adapted for oral administration; solutions and suspensions adapted for parenteral use; and solutions and suspensions adapted for topical ophthalmic or intra-ocular injection. Solutions, suspensions and other dosage forms adapted for topical ophthalmic administration, such as eye drops or tissue irrigating solutions, are particularly preferred for the prevention or treatment of acute or chronic retinal or optic nerve head damage.

The present invention is particularly directed to the provision of compositions adapted for treatment of retinal and optic nerve head tissues. The ophthalmic compositions of the present invention will include one or more AUIs and a pharmaceutically acceptable vehicle. Various types of vehicles may be used. The vehicles will generally be aqueous in nature. Aqueous solutions are generally preferred, based on ease of formulation, as well as a patient's ability to easily administer such compositions by means of instilling one or two drops of the solutions in the affected eyes. However, the AUIs of the present invention may also be readily incorporated into other types of compositions, such as suspensions, viscous or semi-viscous gels or other types of solid or semi-solid compositions. Suspensions may be preferred for AUIs which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

When the AUIs of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85–87 (1990).

The route of administration (e.g., topical, parenteral or oral) and the dosage regimen will be determined by skilled clinicians, based on factors such as the exact nature of the condition being treated, the severity of the condition, and the age and general physical condition of the patient.

As indicated above, use of AUIs to prevent or reduce damage to retinal and optic nerve head tissues at the cellular level is a particularly important aspect of the present invention. Ophthalmic conditions which may be treated include, but are not limited to, retinopathies, macular degeneration, ocular ischemia, glaucoma, and damage associated with injuries to ophthalmic tissues, such as ischemia reperfusion injuries, photochemical injuries, and injuries associated with ocular surgery, particularly injuries to the retina or optic nerve head by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or non-invasive ophthalmic procedures, or other types of surgery.

In general, the doses used for the above described purposes will vary, but will be in an effective amount to prevent, reduce or ameliorate retinal or optic nerve head tissue damage resulting from any of the above listed conditions. As used herein, the term "pharmaceutically effective amount" refers to an amount of one or more AUIs which will prevent, reduce or ameliorate chronic or acute retinal or optic nerve head damage resulting from ischemic or hypoxic conditions in a human patient. The doses used for any of the above-described purposes will generally be from about 0.01 to about 100 milligrams per kilogram of body weight (mg/kg), administered one to four times per day. When the compositions are dosed topically, they will generally be in a concentration range of from 0.001 to about 5% w/v, with 1–2 drops administered 1–4 times per day.

As used herein, the term "pharmaceutically acceptable carrier" refers to any formulation which is safe, and provides the appropriate delivery for the desired route of administration of an effective amount of at least one compound of the present invention.

The following Examples 1 and 2 are formulations useful for intraocular periocular, or retrobulbar injection or perfusion.

| Component | % w/v |
| --- | --- |
| AUI | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |

| Component | % w/v |
| --- | --- |
| AUI | 0.1 |
| Cremophor EL | 10 |
| Tromethamine | 0.12 |

-continued

| Component | % w/v |
| --- | --- |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

EXAMPLE 3

An AUI of the present invention can be formulated in an ocular irrigating solution used during ophthalmic surgery to treat retinal or optic nerve head damage resulting from trauma due to injury or prevent damages resulting from the invasive nature of the surgery. The concentration of the AUI in the irrigating solution will range from 0.001 to 5% w/v The following tablet formulation can be made pursuant to U.S. Pat. No. 5,049,586, incorporated herein by reference.

| Component | % w/v |
| --- | --- |
| Propentofylline | 60 |
| Magnesium oxide | 20 |
| Corn starch | 15 |
| Polyvinylpyrrolidone | 3 |
| Sodium carboxymethylcellulose | 1 |
| Magnesium stearate | 0.8 |

What is claimed is:

1. A method for the treatment of acute or chronic retinal or optic nerve head damage resulting from glaucoma, edema, ischemia, hypoxia or trauma, which comprises administering to a human patient a composition comprising an effective amount of at least one adenosine uptake inhibitor selected from the group consisting of:

dipyridamole, propentofylline, dilazep, nitrobenzylthioinosine,

S-(4-nitrobenzyl)-6-thioguanosine,

S-(4-nitrobenzyl)-6-thioinosine, iodohydroxy-nitrobenzylthioinosine, and analogs, esters, amides and prodrugs thereof, and pharmaceutically acceptable salts therefor; in a pharmaceutically acceptable carrier.

2. The method of claim 1, wherein the adenosine uptake inhibitor is propentofylline.

3. The method of claim 1, wherein the composition is a topical ophthalmic formulation.

4. The method of claim 1, wherein the composition is an periocular, retrobulbar or intraocular injection formulation.

5. The method of claim 1, wherein the composition is a systemic formulation.

6. The method of claim 1, wherein the composition is a surgical irrigating solution.

* * * * *